United States Patent [19]

Mazuel et al.

[11] Patent Number: 4,861,760
[45] Date of Patent: Aug. 29, 1989

[54] OPHTHALMOLOGICAL COMPOSITION OF THE TYPE WHICH UNDERGOES LIQUID-GEL PHASE TRANSITION

[75] Inventors: Claude Mazuel; Marie-Claire Friteyre, both of Riom, France

[73] Assignee: Merck & Co., Inc., Rahway, N.J.

[21] Appl. No.: 911,606

[22] Filed: Sep. 25, 1986

[30] Foreign Application Priority Data

Oct. 3, 1985 [FR] France ................ 85 14689

[51] Int. Cl.⁴ .............. A61K 31/715; A61K 31/70
[52] U.S. Cl. .................... 514/54; 514/912; 514/913; 514/915; 514/944; 536/1.1; 536/114; 536/123
[58] Field of Search .......... 514/54, 944, 912, 913, 514/915, 954; 536/123, 114, 1.1

[56] References Cited

U.S. PATENT DOCUMENTS

| | | | |
|---|---|---|---|
| 2,441,729 | 5/1948 | Steiner | 514/944 |
| 2,935,447 | 5/1960 | Miller et al. | 514/54 |
| 4,013,792 | 3/1977 | Eichman et al. | 574/171 |
| 4,039,662 | 8/1977 | Hecht et al. | 514/54 |
| 4,136,173 | 1/1979 | Pramoda et al. | 514/800 |
| 4,136,177 | 1/1979 | Lin et al. | 514/913 |
| 4,188,373 | 2/1980 | Krezanoski | 514/11 |
| 4,326,052 | 4/1982 | Kang et al. | 536/123 |
| 4,326,053 | 4/1982 | Kang et al. | 536/123 |
| 4,343,787 | 8/1982 | Katz | 514/54 |
| 4,407,792 | 10/1983 | Schoenwald et al. | 514/912 |
| 4,409,205 | 10/1983 | Shively | 514/53 |
| 4,474,751 | 10/1984 | Haslam et al. | 424/78 |
| 4,503,084 | 3/1985 | Baird et al. | 426/573 |
| 4,517,216 | 5/1985 | Shim | 536/1.1 |
| 4,563,366 | 1/1986 | Baird et al. | 426/573 |
| 4,638,059 | 1/1987 | Sutherland | 536/123 |
| 4,661,475 | 4/1987 | Bayerlein et al. | 514/54 |
| 4,717,713 | 1/1988 | Zatz et al. | 514/54 |
| 4,746,528 | 5/1988 | Prest et al. | 536/1.1 |

FOREIGN PATENT DOCUMENTS

| | | | |
|---|---|---|---|
| 1072413 | 2/1980 | Canada . | |
| 134649 | 3/1985 | European Pat. Off. . | |
| 0142426 | 5/1985 | European Pat. Off. | 514/914 |
| 1312244 | 6/1962 | France . | |

OTHER PUBLICATIONS

Jansson et al.; Carbohydrate Research vol. 124:135–139, (1983).

Crescenzi et al.; Carbohydrate Research, vol. 149:425–432, (1986).

Primary Examiner—Ronald W. Griffin
Assistant Examiner—Nancy S. Carson
Attorney, Agent, or Firm—William H. Nicholson; Joseph F. DiPrima

[57] ABSTRACT

The present invention relates to a pharmaceutical composition intended for contacting with a physiological liquid characterized in that said composition is intended to be administered as a non-gelled liquid form and is intended to gel in situ, this composition containing at least one polysaccharide in aqueous solution, of the type which undergoes liquid-gel phase transition gelling in situ under the effect of an increase in the ionic strength of said physiological liquid.

8 Claims, 1 Drawing Sheet

OPHTHALMOLOGICAL COMPOSITION OF THE TYPE WHICH UNDERGOES LIQUID-GEL PHASE TRANSITION

The present invention relates to a pharmaceutical composition containing at least one polysaccharide in aqueous solution, of the type which undergoes liquid-gel phase transition under the effect of an increase in the ionic strength.

The pharmaceutical compositions of the invention are of the type which undergoes liquid-gel phase transition under the effect of an increase in the ionic strength.

They are particularly intended for contacting with physiological liquids. Thus the transition occurs at the contact, as the physiological liquids have a higher tonicity than the one of said compositions.

The compositions of the invention are specially useful for ophtalmic use, but also as injectable form, the formed gel having thus the function of slow-release form, as by intradermic or intramuscular injections, or as galenic form intended for contacting with mucous membranes.

A large percentage of drugs administered to the eye is lost as a result of lacrimal drainage; this applies especially in the case of a liquid formulation. In effect, as a result of this drainage, only a small fraction of the dose administered remains in contact with the cornea for a few minutes, and an even smaller fraction penetrates into the eye.

To overcome this disadvantage, it is known to use viscous solutions, gels, eye ointments or solid eye implants.

Progress has been made in the delivery of drugs by the use of these galenical forms, especially by using the solid implants, by means of which it is possible to reduce greatly the doses of active principle in the formulation while retaining a therapeutic response equivalent to that which would be induced by an eye lotion, the latter, in addition, needing to be administered more frequently.

Some of these implants function by diffusion. Thus, for example, in the "OCUSERT®" system, one weekly application of an oval lens in the conjunctival sac enables an active principle to be delivered by diffusion, but this lens has to be removed after use, which is a source of problems for the patients.

Others function by dissolution, and, in this case, since the implants are either soluble or autodegradable ("LACRISERT®" system), their duration of action is much shorter.

In all cases, the solid implants possess a major disadvantage in that many patients find it difficult to tolerate the introduction into the conjunctival culs-de-sacs of the solid object represented by this implant.

To solve this problem, galenical forms can be used which are liquid at room temperature and assure a semi-solid form at human body temperature. Such delivery systems are described in U.S. Pat. No. 4,188,373, which propose the use of "PLURONIC®" polyols".

These "PLURONIC®" polyols" are thermally gelling polymers in which the polymer concentration is chosen in accordance with the desired liquid-gel transition temperature.

However, with the commercially available "PLURONIC®" polymers", it is difficult to obtain a gel of suitable rigidity while maintaining the transition temperature at physiological temperatures, which are of the order of 25° C.–36° C.

Similarly, Canadian Patent No. 1,072,413 describes systems containing a therapeutic or other agent (poloxamer), the gelification temperatures of which are made higher than room temperature by using additives.

The thermally gelling systems have many disadvantages, including the risk of gelling before administration by an increase in the ambient temperature during packaging or storage, for example.

U.S. Pat. No. 4,474,751 of Merck & Co., relates to other systems for delivering drugs based on thermogelification of gels, but these systems require very large amounts of polymers and this is not always well tolerated by the eye.

The present invention relates to a pharmaceutical composition intended for contacting with a physiological liquid characterized in that said composition is intended to be administered as a non-gelled liquid form and is intended to gel in situ, this composition containing at least one polysaccharide in aqueous solution, of the type which undergoes liquid-gel phase transition gelling in situ under the effect of an increase in the ionic strength of said physiological liquid.

The prefered pharmaceutical composition according to the invention is an ophthalmological composition, the physiological liquid being the lacrimal fluid. Thus, the present invention overcomes these particular problems of administering ophthalmic compositions.

As a matter of fact, the composition, which takes the form of a liquid before its introduction into the eye, undergoes a liquid-gel phase transition, and hence changes from the liquid phase to the gel phase, once it is introduced into the eye, as a result of the ionic strength of the physiological fluid which is in this case, the lacrimal fluid.

This new ophthalmological composition is an amazingly advantageous form for several reasons. In particular, since the presence of lacrimal fluid is required to induce gel formation, any accidental spillage of solution outside of the eye cannot result in gel formation. Furthermore, in contrast to the thermally gelling systems, an increase in the ambient temperature cannot result in the solution gelling during storage.

Also, the polymer used can form a gel at concentrations 10- to 100- fold lower than those used in systems involving thermogelification. It is hence very well tolerated by the eye.

Finally, when these compositions contain a pharmaceutically active substance, such a delivery system makes it possible to achieve great bioavailability of the product, and concentrations of active principle which are sustained with time, advantages of a slow delivery system.

Furthermore, in the case of already gelled or semi-solid compositions, it is not possible to administer them by volumetric means, especially when they come from a multi-dose container. To administer these in reproducible quantities, one is then compelled to employ gravimetric means.

The compositions according to the invention have, on the one hand, the advantage of liquid ophthalmic compositions, namely reproducible and accurate dosing, by volumetric means, of the active substance, and on the other hand the advantages known for the systems in rigid or semisolid gel form, relating to the delivery of active substances.

The composition according to the invention consequently has neither the disadvantages of losses of active substances characteristic of simple liquid compositions, nor the unpleasant aspects of solid implant systems, nor finally the difficulties of administration associated with gelled or semi-solid compositions.

The Applicant Company has demonstrated that aqueous polysaccharide solutions, of the type which undergoes liquid-gel phase transition under the effect of an increase in the ionic strength, and are especially suitable according to the invention, are solutions of a polysaccharide obtained by fermentation of a microorganism.

Thus, according to the invention, an extracellular anionic heteropolysaccharide elaborated by the bacterium *Pseudomonas elodea* and known by the name gellan gum is preferably used.

This polysaccharide, manufactured by KELCO & CO., is already used as a gelling agent for culture medium and also in food products. The structure of this heteropolysaccharide consists of the following tetrasaccharide repeating unit:

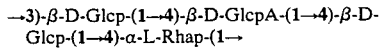

which may, or may not, be partially 0-acetylated on its $\beta$-D-glucopyranose ($\beta$-D-Glcp) residues.

The preparation of such polysaccharides in native and deacetylated form is described, in particular, in U.S. Pat. Nos. 4,326,053 and 4,326,052 of MERCK & CO., Inc. Rahway N.J., and their structure has been described, in particular, by JANSSON & LINDBERG, Carbohydr. res. 124 (1983) 35–9.

According to the present invention, aqueous solutions containing about 0.1% to about 2.0% by weight of gellan gum, and especially of the product known by the tradename Gelrite ®, which is a low acetyl clarified grade of gellan gum, are viscous at low ionic strength but undergo a liquid-gel transition when the ionic strength is increased, and this is the case when this aqueous solution is introduced into the eye.

The rigidity of the gel can be modified by adjusting the polymer concentration.

The gellan gum product not only has the property of changing form the liquid to the solid phase when placed in a medium of higher ionic strength, but it also possesses two advantageous additional properties according to the present invention.

In effect, Gelrite ® in aqueous solution is thixotropic (FIG. 1) and thermoplastic (FIG. 2).

These two properties enable its fluidity to be increased by shaking or slightly warming the sample before administration to the eye.

(1) in distilled water;
(2) in a simulated tear fluid.

Figure 1:
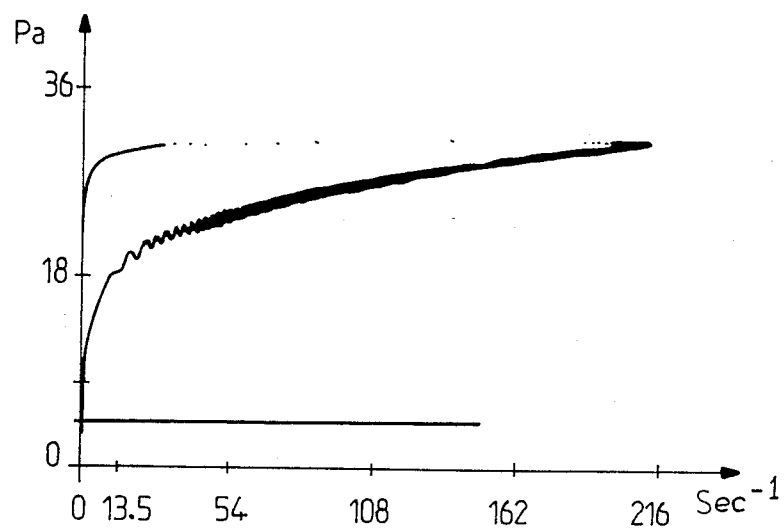
FIG. 1 shows the rheology of a 0.6% aqueous solution of Gelrite ® at 20° C. (shear stress (Pa) versus shear rate (Sec$^{-1}$)).
Figure 2:
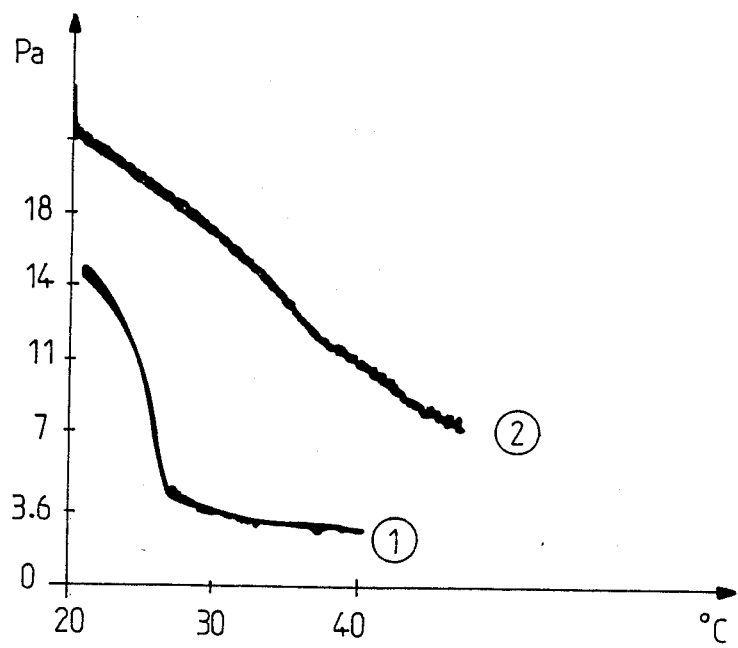
FIG. 2 shows the shear stress (Pa) versus temperature (°C.) behavior [at a constant shear rate of 86 second$^{-1}$] of a 0.6% Gelrite ® solution, after a 30% dilution.

This latter case of FIG. 2 (2) shows the increase in viscosity resulting from the dilution of Gelrite ® in a simulated lacrimal fluid.

Thus, the Applicant Company has demonstrated gel formation in a rabbit's eye following a 20 μl instillation of a solution containing 0.4% by weight of Gelrite ® deionized water.

The ophthalmic compositions according to the invention can be used as they are in various applications, and, for example, to maintain adequate hydration of the eye (treatment of dry eye syndrome).

Furthermore, it appears that the ophtalmic compositions according to the invention are especially suitable for administering to the eye any pharmaceutically active substance administered for curative and/or diagnostic purposes. Thus, the present invention relates to a pharmaceutical composition which contains at least one pharmaceutically active substance for curative or diagnostic purposes.

By pharmaceutically active substance, there is understood one or more drugs and/or one or more diagnostic agents. Any active substance can be delivered by the compositions according to the invention. The active substance is preferably chosen to be soluble in water, although some active substances show greater solubility than others in the aqueous polysaccharide solutions according to the invention. Furthermore, active substances can be in suspension or in emulsion (e.g. emulsions of oil droplets, complex lipidic materials, liposomes) in the aqueous polysaccharide solutions. Therefore, the present invention relates to ophthalmic compositions containing at least one active substance in solution or suspension or emulsion in the aqueous polysaccharide solution.

The prefered pharmaceutically active substance, used according to the present invention is timolol or one of its derivatives.

Timolol can be used alone or in combination with other pharmaceutically active agents.

The present invention relates to the ophthalmic compositions preferably containing about 0.1% to about 2.0% by weight of the polysaccharide described above, and about 0.001% to about 5% by weight of at least one pharmaceutically active substance.

The quantities relating to the aqueous gellan gum solution make it possible to obtain a suitable gel consistency and to compensate the loss induced by the sterilization procedures used during the process of manufacture of these ophthalmic compositions.

Other additives can also take part in the ophthalmic compositions according to the invention. These are, in particular, other polymers suitable for topical application to the eye, small amounts of acids or bases for adjusting the pH to values suitable for administration to the eye, nonionic tonicity adjusting agents, surfactants, agents for controlling bacterial contamination or, for example, other additives for solubilization or stabilization of the active substance, or any other additive which assist in the formulation.

If necessary, the gel-inducing effect of ionized active substances, for example, which are incorporated in the compositions according to the invention, can be neutralized by adding to the formulation a suitable ion pair-forming agent.

For example, the slight gelling effect induced by adding 0.1 mg/ml of benzalkonium chloride in a Gelrite ® solution according to the invention can be eliminated by adding a small amount of acetic acid. The Applicant Company has in addition demonstrated that Gelrite ® solutions according to the invention are compatible with other formulation ingredients such as various buffers and potential ion pair-forming agents.

As will emerge in the examples, mannitol can be used in the compositions according to the invention in order to regulate the tonicity of the medium without changing the gelling properties.

Other tonicity adjusting agents can be used, sorbitol or any sugar for example.

For their administration to the eye, the ophthalmic compositions according to the invention are administered in liquid form, by any conventional means for delivering drops, such as an eye-dropper or, for example, the so called "OCUMETER®" system.

The compositions according to the invention can be administered in the usual manner for eye lotions, in the inferior cul-de-sac of the conjunctiva on the outside of the eye.

By way of example, a drop of liquid composition containing about 25 mg of ophthalmic composition enables about 0.0025 mg to about 1.25 mg of active substance to be administered.

The active substances, or drugs, or diagnostic agents, used in the pharmaceutical compositions according to the invention are preferably suited to the treatment of the disease from which the patient is suffering and/or to the diagnostic method which it is desired to employ.

For example, if the patient is suffering from glaucoma, the active substance chosen in preferably a beta blocker such as timolol or one of its derivatives.

Toxicological studies prove the good tolerability of gellan gums: acute oral toxicity tests in rats show that the lethal dose 50 ($LD_{50}$) is greater than 5000 mg per kg; acute toxicity tests by inhalation show that exposure of rats for 4 hours to a nominal concentration of 6.09 mg/l does not cause the death of any animal in a group of 10 animals, which indicates that the lethal concentration 50 ($LC_{50}$) is greater than 6.09 mg/l.

DRAIZE-type eye irritation tests in rabbits show that the product is not regarded as an eye irritant.

When these compositions contain an active substance, the objective of such a system for delivering the active substance is to achieve great bioavailability of the substance and concentrations of this substance which are sustained with time.

The drugs or diagnostic agents which can be administered by means of the ophthalmic compositions according to the invention are, for example:

antibacterial substances such as beta-lactam antibiotics, such as cefoxitin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides:

aminoglycoside antibiotics such as gentamycin, kanamycin, amikacin, sisomicin and tobramycin:

nalidixic acid and its analogs such as norfloxacin and the antimicrobial combination fluoroalanine/pentizidone, nitrofurazones and analogs thereof:

antihistaminics and decongestants such as pyrilamine, chlorpheniramine, tetrahydrazoline, antazoline and analogs thereof:

anti-inflammatories such as cortisone, hydrocortisone, hydrocortisone acetate, betamethasone, dexamethasone, dexamethasone sodium phosphate, prednisone, methylprednisolone, medrysone, fluorometholone, prednisolone, prednisolone sodium phosphate, triamcinolone, indomethacin, sulindac, its salts and its corresponding sulfides, and analogs thereof:

miotics and anticholinergics such as echothiophate, pilocarpine, physostigmine salicylate, diisopropylfluorophosphate, epinephrine, dipivaloylepinephrine, neostigmine, echothiopate iodide, demecarium bromide, carbamoyl choline chloride, methacholine, bethanechol, and analogs thereof:

mydriatics such as atropine, homatropine, scopolamine, hydroxyamphetamine, ephedrine, cocaine, tropicamide, phenylephrine, cyclopentolate, oxyphenonium, eucatropine, and analogs thereof:

other drugs used in the treatment of conditions and lesions of the eyes such as:

antiglaucoma drugs for example timolol, and especially its maleic salt and R-timolol and a combination of timolol or R-timolol with pilocarpine, as well as many other adrenergic agonists and/or antagonists: epinephrine and an epinephrine complex, or prodrugs such as bitartrate, borate, hydrochloride and dipivefrine derivatives and hyperosmotic agents such as glycerol, mannitol and urea: carbonic anhydrase inhibitors such as acetazolamide, dichlorphenamide, 2-(p-hydroxyphenyl)-thio-5thiophenesulfonamide, 6-hydroxy-2-benzothiazolesulfonamide; and 6-pivaloyloxy-2-benzothiazolesulfonamide antiparasitic compounds and/or anti-protozoal compounds such as ivermectin, pyrimethamine, trisulfapidimidine, clindamycin and corticosteroid preparations;

compounds having antiviral activity such as acyclovir, 5-iodo-2'-deoxyuridine (IDU), adenosine arabinoside (Ara-A), trifluorothymidine, and interferon and interferon-inducing agents such as poly I:C;

antifungal agents such as amphotericin B, nystatin, flucytosine, natamycin and miconazole:

anesthetic agents such as etidocaine cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine:

ophthalmic diagnostic agents, such as:
(a) those used to examine the retina such as sodium fluorescein;
(b) those used to examine the conjunctiva, cornea and lacrimal apparatus, such as fluorescein and rose bengal: and
(c) those used to examine abnormal pupillary responses such as methacholine, cocaine, adrenaline, atropine, hydroxyamphetamine and pilocarpine:

ophthalmic agents used as adjuncts in surgery, such as alpha-chymotrypsin and hyaluronidase:

chelating agents such as ethylenediaminetetraacetic acid (EDTA) and deferoxamine:

immunosuppressants and anti-metabolites such as methotrexate, cyclophosphamide, 6-mercaptopurine and azathioprine: and combinations of the compounds mentioned above, such as antibiotics/antiinflammatories combinations such as the combination of neomycin sulfate and dexamethasone sodium phosphate, and combinations concomitantly treating glaucoma, for example a combination of timolol maleate and aceclidine.

Generally, the tears produced by the eye dilute the active substance and very rapidly deplete the dose of active substance administered by conventional liquid solutions.

The compositions containing a polysaccharide in aqueous solution according to the invention, of the type which undergoes liquid-gel phase transition under the effect of an increase in the ionic strength, are diluted less rapidly and make it possible to obtain a sustained delivery of the active substance dissolved or suspended in the composition. (To this end, the total ionic strength of the formulation must be kept as low as possible). This prolonged residence time, permitted by the composition according to the present invention, leads to more effective levels of concentration of active substance in the lacrimal film.

A test which demonstrated the prolonged presence of the active substance after instillation in the eye of a composition according to the invention, and also other characteristics and advantages of the present invention, appear in the Examples and Figures which follow, which illustrate the invention (the percentages being given by weight).

EXAMPLE 1

Simple ophthalmic composition

|  | Solution 1 | Solution 2 | Solution 3 |
|---|---|---|---|
| Gelrite ® | 0.6% | 0.6% | 0.2% |
| benzalkonium chloride | 0.01% | 0.005% | — |
| mannitol | 4% | 4% | — |
| sufficient water to make | 100% | 100% | 100% |

EXAMPLE 2

Composition for delivering timolol

|  | Solution 1 | Solution 2 | Solution 3 |
|---|---|---|---|
| timolol maleate | 0.34% | 0.65% | 0.34% |
| Gelrite ® | 0.6% | 0.6% | 0.6% |
| benzalkonium chloride | 0.01% | 0.01% | — |
| mannitol | 4% | 4% | 4% |
| sufficient water to make | 100% | 100% | 100% |

EXAMPLE 3

Composition for delivering dexamethasone phosphate

|  | Solution 1 | Solution 2 | Solution 3 |
|---|---|---|---|
| dexamethasone phosphate | 0.1% | 0.05% | 0.1% |
| Gelrite ® | 0.6% | 0.3 % | 0.6% |
| benzalkonium chloride | 0.01% | 0.01% | 0.01% |
| mannitol | 4% | 4% | 4% |
| sufficient water to make | 100% | 100% | 100% |

EXAMPLE 4

To demonstrate the prolonged presence of the active substance in the eye, after instillation of the active substance incorporated in a composition according to the invention, a comparative test was performed.

The removal of fluorescein from the conjunctival sac of rabbits after an installation of fluorescein solution, either in distilled water or in a vehicle containing 0.6% Gelrite ®, was observed by far UV radiation.

In the eyes treated with the aqueous solution, no fluorescein remains 3 hours after the instillation, whereas in the eyes treated with the vehicle containing the Gelrite ®, fluorescein is still persisting 5 hours after the instillation.

EXAMPLE 5

Composition for delivering timolol

Studies are carried out in vivo to obtain data concerning the timolol bioavailability from the solution 1 of example 2. The concentration of timolol in aqueous humor of non-anaesthetized Albino Rabbits is valued. Single 50 $\mu l$ Instillations of Gelrite ® Formulations (Example 2 solution 1) and Timoptic ® commercial solutions, each Containing 0.25% of timolol are carried out for a comparison purpose. The Gelrite ® Solutions were Made with 3 Different lots of Gelrite ® Polymers. The obtained results are shown in the following table:

| Time after instillation in minutes | Concentration of Timolol in Aqueous Humor in ug/ml ± S.E.M. (N) | | | | |
|---|---|---|---|---|---|
|  | GELRITE FORMULATION | | | Average | |
|  | Lot 001 | Lot 002 | Lot 003 | Gelrite | TIMOPTIC |
| 30 | 4.1 ± 0.6 (8) | 3.0 ± 0.3 (20) | 3.2 ± 0.4 (8) | 3.4 ± 0.2 (36) | 1.1 ± 0.1 (20) |
| 60 | 2.3 ± 0.4 (8) | 2.9 ± 0.3 (20) | 3.0 ± 0.2 (8) | 2.7 ± 0.2 (36) | 0.9 ± 0.3 (16) |
| 120 | 1.1 ± 0.2 (4) | 1.6 ± 0.2 (16) | 1.1 ± 0.1 (8) | 1.3 ± 0.03 (28) | 0.4 ± 0.05 (8) |
| 180 | 1.0 ± 0.2 (4) | 0.8 ± 0.1 (16) | 0.6 ± 0.05 (8) | 0.8 ± 0.06 (28) | 0.3 ± 0.04 (12) |

Note:
S.E.M. = Standard Error of Mean
N = Number of eyes tested

The invention is not limited to the above examples; the compositions of the invention are also useful for their application in all pharmaceutical compositions, which are intended for contacting with the physiological liquids.

Thus, the present invention also concerns the injectable compositions, for intradermic or intramuscular injections, and external topical compositions which are intended for contacting with mucous membranes.

We claim:

1. A liquid aqueous ophthalmological composition comprising 0.1 to 2% by weight of gellan gum which on administration to the eye changes from a liquid to a gel as a result of the ionic strength of the lacrimal fluid.

2. The composition of claim 2 which additionally comprises about 0.001% to 5% by weight of an ophthalmic pharmaceutically-active substance.

3. The composition of claim 2 wherein the pharmaceutically-active substance is selected from the group consisting of an antibacterial substance and an anti-glaucoma drug.

4. The composition of claim 3 wherein the antibacterial substance is norfloxacin and the antiglaucoma drug is timolol maleate or a carbonic anhydrase inhibitor.

5. The composition of claim 1 wherein the gellan gum is Gelrite.

6. The composition of claim 5 which additionally comprises about 0.001% to 5% by weight of an ophthalmic pharmaceutically-active substance.

7. The composition of claim 6 wherein the pharmaceutically-active substance is selected from the group consisting of an antibacterial substance and an antiglaucoma drug.

8. The composition of claim 7 wherein the antibacterial substance is norfloxacin and the antiglaucoma drug is selected from the group consisting of timolol maleate and a carbonic anhydrase inhibitor.

* * * * *

UNITED STATES PATENT AND TRADEMARK OFFICE
CERTIFICATE OF CORRECTION

PATENT NO. : 4,861,760
DATED : August 29, 1989
INVENTOR(S) : C. Mazuel; M. Friteyre It is certified that error appears in the above-identified patent and that said Letters Patent is hereby corrected as shown below:

On the title page:

In the Assignee:

Change "Merck & Co., Inc." to --Laboratoires Merck Sharp & Dohme-Chibret--.

Signed and Sealed this

Twenty-second Day of May, 1990

Attest:

HARRY F. MANBECK, JR.

Attesting Officer     Commissioner of Patents and Trademarks